United States Patent [19]

Chen et al.

[11] Patent Number: 4,460,364

[45] Date of Patent: Jul. 17, 1984

[54] PRESSURE SENSITIVE HOT MELT ADHESIVE FOR SANITARY PRODUCTS

[75] Inventors: Franklin M. C. Chen, Kendall Park; Archie L. Jones, Somerset, both of N.J.

[73] Assignee: Personal Products Company, Milltown, N.J.

[21] Appl. No.: 411,931

[22] Filed: Aug. 26, 1982

[51] Int. Cl.³ .................. A61F 13/16; C08L 53/00
[52] U.S. Cl. .................. 604/387; 524/505; 604/389
[58] Field of Search .............. 604/387, 389; 525/88; 524/505

[56] References Cited

U.S. PATENT DOCUMENTS

| | | | |
|---|---|---|---|
| 3,787,531 | 1/1974 | Dahlquist et al. | 525/88 |
| 3,897,783 | 8/1975 | Ginocchio | 604/387 |
| 4,136,699 | 1/1979 | Collins et al. | 604/387 |
| 4,186,743 | 2/1980 | Steiger | 604/387 |
| 4,259,230 | 3/1981 | Bunnelle et al. | 524/505 |

*Primary Examiner*—Allan Lieberman
*Attorney, Agent, or Firm*—Jason Lipow

[57] ABSTRACT

A hot melt pressure-sensitive adhesive is provided which is selected to exhibit critical rheological properties which manifest themselves into the desired performance criteria of tenacious bonding and clean release.

6 Claims, 1 Drawing Figure

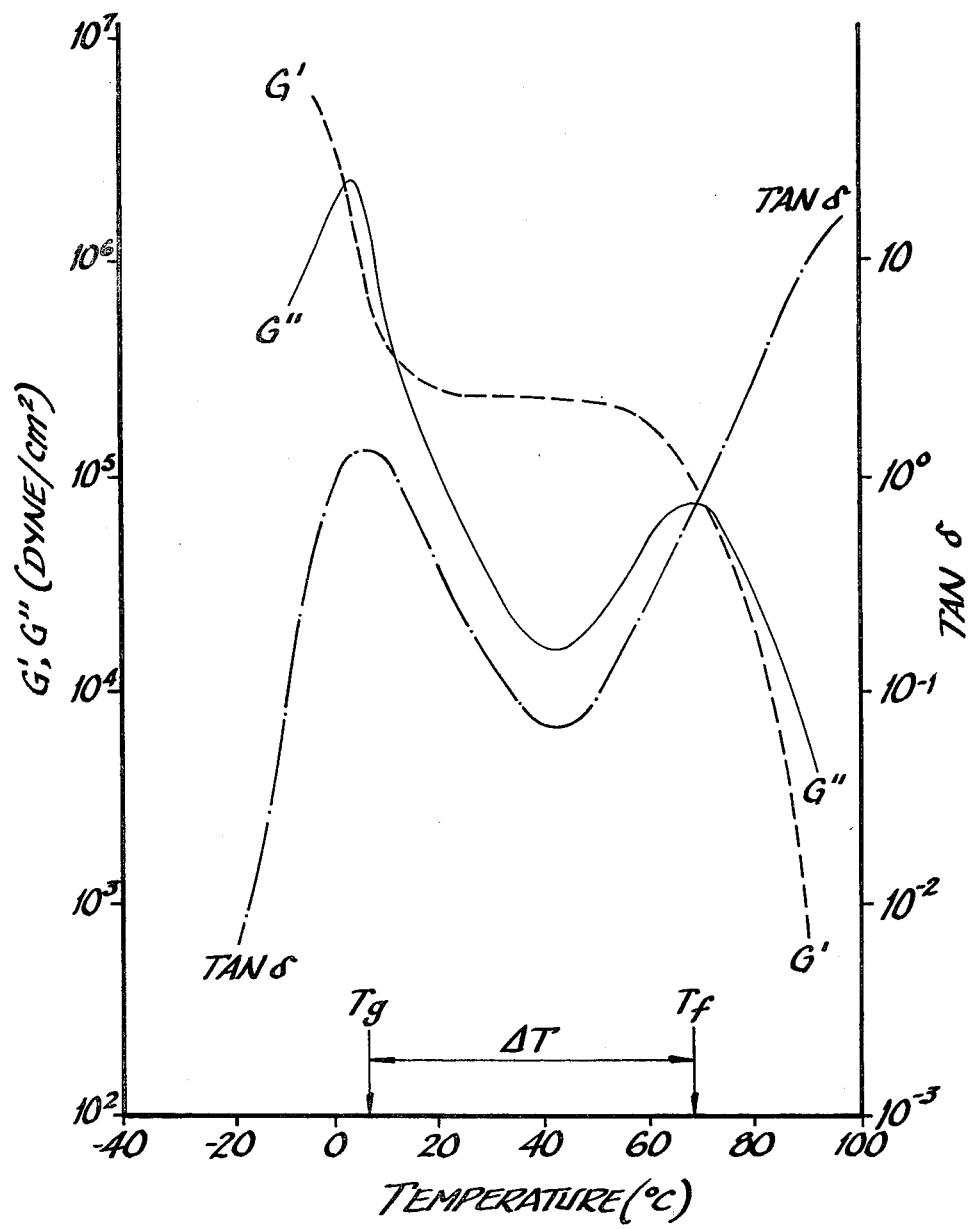

PRESSURE SENSITIVE HOT MELT ADHESIVE FOR SANITARY PRODUCTS

BACKGROUND OF THE INVENTION

This invention relates to pressure-sensitive adhesive compositions and more particularly to compositions which are applied to a substrate in the hot or molten state and which cool into a relatively tacky pressure-sensitive adhesive. Accordingly, the substrate can be adhered to another surface by the application of pressure and may subsequently be removed by being peeled from this surface.

In a specific embodiment, this invention is related to hot melt pressure-sensitive adhesives applied to the surface of articles for absorbing and retaining body fluids such as diapers, sanitary napkins and bandages. In the case of sanitary napkins, for example, the napkin has a body facing side and a garment facing side. Pressure-sensitive adhesive is applied to the garment facing side and attaches the napkin to the crotch portion of an undergarment whereby the napkin stays in place while in use. In such case, it is, of course, desirable that the napkin adhere tenaciously to the undergarment after being pressed into place so that the napkin does not shift or detach under the normal stresses exerted on the adhesive bond by virtue of the usual body movements of the wearer. On the other hand, it is important that the napkin release cleanly from the undergarment after use without leaving any residue on the undergarment.

The art is now replete with formulations for pressure-sensitive adhesives for use in such body exudate absorbing products as sanitary napkins. These prior suggestions can generally be classified into two groups; namely, the water based adhesive systems and the so-called hot melt systems. Several drawbacks have been encountered in the use of these prior systems in attempts to meet the criteria set out above of tenacious bonding and clean release.

Specifically, the water based systems have suffered from the problem of slow dry down or slow set. Basically, these water based systems require, initially, a high water content in order for them to have sufficient liquid flow characteristics to be applied to a substrate at the high production speeds required for the economical manufacture of such disposable products as sanitary napkins and diapers. Unfortunately, this high water content has necessitated a concommitent long dry down or set time which in turn has slowed down the production process.

In an attempt to cure this problem, the art has turned to the so-called hot melt pressure-sensitive adhesive systems, the principle ingredients of which are thermoplastic rubbery polymers in combination with plasticizing oils, tackifiers, fillers, pigments, antioxidants and other stabilizers. Such hot melt adhesive formulations are exemplified by U.S. Pat. No. 4,136,699 issued on Jan. 30, 1979 to J. A. Collins, et al.; U.S. Pat. No. 3,554,940 issued on Jan. 12, 1971 to M. Arakawa, et al.; U.S. Pat. No. 3,917,607 issued to R. K. Crossland, et al. on Nov. 4, 1975; U.S. Pat. No. 3,239,478 issued to Harlan, Jr. on Mar., 1966; U.S. Pat. No. 3,686,107 issued on Aug. 22, 1972 to T. Russell; U.S. Pat. No. 3,862,068 issued on Jan. 21, 1975 to T. Russell; U.S. Pat. No. 3,954,692 issued on May 4, 1976 to R. E. Downery; U.S. Pat. No. 3,935,338 issued on Jan. 27, 1976 to W. J. Robinson, et al.; U.S. Pat. No. 3,932,327 issued on Jan. 13, 1976 to F. Naylor; U.S. Pat. No. 3,956,223 issued on May 11, 1976 to J. Chiang; and U.S. Pat. No. 4,028,292 issued on June 7, 1977 to R. Korpman. In each of these prior art suggestions, the proportions of ingredients, molecular weights and chemical nature of the various additives are all selected to produce an adhesive composition which has sufficient flow properties when heated to be applied to a substrate and which can rapidly cool to a pressure-sensitive adhesive that will bond such substrates to another with a satisfactory degree of tenacity. Unfortunately, to date these prior suggestions, while representing an improvement over water based pressure-sensitive adhesives, have at best represented a compromise between tenacity and clean release. Generally, to obtain clean release, as from an undergarment as is the case for adhesively attached sanitary napkins, tenacity has been sacrificed.

SUMMARY OF THE INVENTION

It has now been discovered that a hot melt pressure-sensitive adhesive may be provided which is "tailor-made" to cure the deficiencies of prior art compositions by being specifically selected to exhibit certain rheological properties which manifest themselves into the desired performance criteria; namely, tenacious bonding and clean release.

Specifically, it has been discovered that an adhesive formulation may be selected on the basis of a readily available sheer stress-strain analysis by the identification of those rheological properties which are particularly applicable to the dynamics of bonding a pressure-sensitive hot melt adhesive to a substrate and subsequently peeling such hot melt from the substrate. Recognition has now been taken of the fact that the bonding process is a relatively slow one in which stress is applied over a relatively long period of time and elastic recovery, after such stress is applied, may take place also over a long period of time. On the other hand, in the peeling operation, stress is applied rapidly and elastic recovery must be realized in a short time interval. Said in other words, it is important that the viscoelastic materials chosen for use as a hot melt composition behave, under dynamic sheer stress conditions, as a relatively viscous material when under a prolonged stress and provided with a long recovery time. At the same time, this viscoelastic material must be selected to exhibit elastic properties when under dynamic sheer stresses imposed rapidly and when provided with only a short recovery time.

In accordance with this invention the selection of a satisfactory adhesive may be made by performing an analysis of the composition's rheological properties by use of a readily available analytical instrument for characterizing viscoelastic materials; namely, a Thermomechanical Spectrometer. Basically, this instrument is designed to impose on the sample being tested a selected strain which varies with the temperature of the sample in a known manner e.g., sinusoidally. The stress function related to this strain is sensed by the instrument and the stress-strain relationships are interpreted by an integral microprocessor and reported graphically as such temperature dependant rheological functions as the storage modules, the loss modulus, and the ratio of the two moduli, known as the Tan δ. These parameters, as a function of temperature are, in fact, the analog of the same parameters as a function of time based on the well known rheological time-temperature superposition principle. Accordingly, the parameters generated by the Thermomechanical Spectrometer describe the stress-strain properties of a given material under dynamic conditions.

It has been discovered that a hot melt adhesive which exhibits certain critical parameters by Thermomechanical Spectrometer analysis is uniquely suited for the purpose of meeting the criteria of tenacious bond and clean release and, with respect to these criteria, will represent a substantial improvement over hot melt compositions now known in the art. In particular, it has been discovered that the hot melt adhesive composition should be selected to have a glass transition temperature of the rubbery phase which lies between 0° and 10° C. Further, the composition should exhibit a temperature difference between the glass temperature of the rubbery phase and the flow temperature of between 45° C. and 55° C. The storage modulus between the glass transition temperature of the rubbery phase and the flow temperature should be a monotonic decreasing function of temperature and should have a value, at the arithmetic average between the glass transition temperature of the rubbery phase and the flow temperature ranging from $3.5 \times 10^5$ to a $6.5 \times 10^5$ dynes per cm$^2$. Still further, the slope of the function log$_{10}$ of the storage modulus (in dynes/cm$^2$) verses temperature (in ° C.) should, at a temperature equal to the arithmetic average of the glass transition temperature of the rubbery phase and the flow temperature, range from $-0.005$ to $-0.025$.

It should be understood that the above set out parameters are defined in terms of the mechanical spectrometer test analysis conducted under the conditions hereinafter set out.

The selected formulations must also exhibit stable properties and not be subject to degradation, as for example by oxidation, over a substantial time period. Accordingly, the composition should exhibit no substantial viscosity reduction when held for a period of ninety hours at 350° F. (176.7° C.) in an air environment. Needless to say, the components chosen for a specific composition meeting the above set out rheological properties must also be compatible with each other to the degree that a homogeneous mixture may be prepared and maintained. Said in other words, the adhesive properties of the surface of a mass of the adhesive composition should not signicantly vary from that of the bulk of the mass.

When the above set out parameters are met, the adhesive in question has been found to combine high tenacity and clean peel to a degree unsurpassed by any composition known heretofore while still capable of being stored in a molten state for a period of time without unacceptable degradation.

BRIEF DESCRIPTION OF THE DRAWINGS

The invention will be best understood by a consideration of the following description taken together with the appended drawing which is a typical rheological analysis as generated by a Thermomechanical Spectometer illustrating the storage modulus, the loss modulus and tan $\delta$ as functions of temperature.

DETAILED DESCRIPTION OF THE INVENTION

As hereinabove described, this invention comprises the selection, from a wide variety of available viscoelastic polymeric compositions, of one which is particularly suited to meet the requirements of tenacious bond and clean release and further, will not degrade with time.

The viscoelastic polymer of choice, as the principle ingredient in the formulation of this invention, is of the A-B-A block copolymer type and specifically of the type wherein the midblock (i.e., the "B" portion) comprises polyolefins such as, for example, copolymers of ethylene and butylene. The end block (the "A" portion) comprises polystyrene.

A wide variety of the rubbery copolymers are available from the Shell Oil Company and are sold by them under the trademark "KRATON" and in particular under the tradename "KRATON G". The KRATON G series of rubbery polymers are available in a wide range of number average molecular weights and weight ratios of end to midblock groups. For example KRATON G is available wherein the number average molecular weights of the individual A blocks range from about 7000 to about 30,000 and the A-blocks may constitute from about 10–50% by weight of the block copolymer. Within this wide scope of available KRATON G type polymers, materials may be selected to produce a full spectrum of rheological properties in adhesives ranging from relatively elastic to relatively viscous flow properties under static conditions and at a given temperature.

In selecting a satisfactory viscoelastic material, the user is faced with the problem of performing many empirical experiments before a selection can be arrived at. This problem is greatly aggravated when the ultimate use is for adhesive behavior under varying dynamic conditions such as is faced, for example, when selecting a satisfactory viscoelastic material for use in a sanitary napkin. Generally, for such use the adhesive composition is applied by the manufacturer in the molten state to the garment facing outer surface of a napkin and covered with a protective release strip. The user, immediately prior to use, removes the release strip and presses the napkin into place against the inside crotch surface of an undergarment. The adhesive, under the influence of the stress exerted upon it by the user's pressing the napkin in place, deforms and flows into the garment surface irregularities bonding therewith. Upon the release of the user applied stress, the adhesive recovers and, with the passage of time, reaches an "equilibrium" state of deformation which, for all practical purposes, is constant although it should be understood that further recovery, albeit small, is most likely still occurring. Ideally, to maximize the tenacity of the bond, extremely slow recovery is desirable with the equilibrium state being achieved at a low percent recovery In removing the napkin from the garment, the user generally grips an end of the napkin and rapidly peels the napkin from the undergarment thereby applying a rapid stress to the adhesive. Ideally under these conditions of rapid deformation, it is desirable that the recovery from the resulting deformation be equally rapid i.e., that the adhesive layer possesses sufficient cohesive strength assuring a clean release from the garment.

The problem of adhesive formulation has been even further compounded by the fact that while a composition may at a given point in time exhibit an approximation of the ideal rheological properties described above, with the passage of time, these properties may change as the polymers degrade or oxidize when exposed to an air atmosphere. There is then no assurance that consistent in-use performance can be maintained.

It has now been discovered that the extremely difficult task of selecting a satisfactory composition from the wide range of KRATON G adhesive compositions by empirical experiment has now been greatly facilitated by our discovery that the desired ideal behavior corresponds to certain critical rheological time dependent properties of the adhesive composition. Further, the properties have enabled us to define an adhesive composition which, in use, far surpasses the in-use performance of any known prior composition derived by experimentation. Our new adhesive composition is characterized by certain basic rheological time dependent properties determined by use of a Thermomechanical Spectrometer. This analysis is designed to describe the characteristics of a viscoelastic material and to take into account the phase shift between stress and strain. By use of the time-temperature superposition principal, the time varient is analogized to a temperature varient which can conveniently be measured.

With a degree of simplification being understood, when a given stress is applied, as a function of time, upon a viscoelastic material, the corresponding deformation or strain tends to lag the stress function. Accordingly, if the time dependent strain $\epsilon(t)$ is a sinusoidal function of time such that:

$$\epsilon(t) = \epsilon_m \sin(\omega t)$$

wherein $\epsilon_m$ is the amplitude, t is the time and $\omega$ is the angular velocity in radians per unit time, then the correspond time dependent stress, $\sigma(t)$, will also be sinusoidal but will lag by an angle $\delta$ such that:

$$\sigma(t) = \theta_m \sin(\omega t + \delta)$$

which can be expanded to:

$$\sigma(t) = \sigma_m \cos \delta \sin(\omega t) + \sigma_m \sin \delta \cos(\omega t)$$

$$= \frac{\epsilon m}{\epsilon m} \sigma_m \cos \delta \sin(\omega t) + \frac{\epsilon m}{\epsilon m} \sigma_m \sin \delta \cos(\omega t)$$

$$= \epsilon_m G' \sin(\omega t) + \epsilon_m G'' \cos(\omega t) \text{ ; where}$$

$$G' = \frac{\sigma m}{\epsilon m} \cos \delta \text{ and } G'' = \frac{lm}{\epsilon m} \sin \delta;$$

and wherein, for a given sample, at a given temperature, stressed sinusoidally at a constant angular velocity, then G' and G'' will be unique functions of time. The paramater G' is termed the storage modulus and G'' is termed the loss modulus. The ratio of G''/G' is termed tan $\delta$. Based on the above it can be seen that the dynamic properties of an adhesive can be determined by determining the time dependent functions G', G'' and tan $\delta$. In order to get a full definition of these functions by experiment, an inconveniently long time span is required and so a time varying study is impractical. Fortunately, it has been discovered that these time dependent functions have a direct analog in temperature related functions in accordance with the well known time-temperature Superposition Principle (as discussed, for example, in Rheology, Vol. 2, edited by Frederick R. Eirich, 1958 Academic Press, Inc., N.Y. at p. 67). In the simplest form of this principle, curves of these functions and the $\log_{10}$ of these functions, plotted as the ordinate vs $\log_{10}$ time plotted is the abscissa may be superimposed with an abscissa reading in log of the temperature without changing the characteristics of the curves. Accordingly, a long time interval is equivalent to a high temperature and a short time interval is equivalent to a low temperature.

The Thermomechanical Spectrometer makes use of this time-temperature superposition principle by substituting a temperature history for a time history. In its use, the sample to be tested is placed between two parallel plates and a strain is imposed which may be selected to vary sinusoidally with temperature. Temperature is controlled during the test by using convected gas in an environmental chamber. The oscillation frequency may be selected as an arbitrary constant value. The Spectrometer is provided with a transducer which, in effect, senses the torque and normal force generated in response to the imposed strain. These sensed forces are translated, by the use of a microcomputer integral with the Spectrometer, into stresses which in turn are translated by the logic of the microcomputer software into the rheological functions of G', G'' and tan $\delta$.

The appended drawing illustrates the rheological functions of temperature (as an analog of time) as calculated from Thermomechanical Spectrometer analysis, for an adhesive composition which meets the prescribed criteria of this invention. As is illustrated by this drawing, the adhesive behaves quite differently at low temperatures (short time increments) as compared to high temperatures (long time increments). Specifically, the material varies from the glassy state to a rubbery elastic state to a viscous flow state as the temperature is increased from below $T_g$ to above $T_f$.

Certain rheological properties may be defined from these functions. Accordingly, the temperatures at which the tan $\delta$ function reaches a maximum is termed the glass transition temperature of the rubbery phase of the composition i.e., the mid-block glass transition temperature, $T_g$. The temperature at which the function G'' reaches its second maximum is the flow temperature, $T_f$. Between $T_g$ and $T_f$ is a temperature range herein referred to as the rubbery plateau region.

It has been discovered that if an adhesive composition based on the A-B-A KRATON G type polymer is selected on the basis of exhibiting certain of the above described rheological properties lying within narrow ranges, then the desired end use criteria of tenacious bonding and clean release can be realized, provided the further selection is made in choosing a composition which will maintain these properties over the expected shelf life of the chosen composition. Specifically, under the parameter of the Mechanical Spectrometer analysis described herein, it has been discovered that the glass transition temperature of the rubbery phase ($T_g$) must lie between 0° C. and 10° C. The rubbery plateau region, the region between the glass transition temperature of the rubber phase ($T_g$) and the flow temperature ($T_f$), must extend for a temperature interval of from 45° C. to 55° C. The storage modulus, G' must be a monotonic decreasing function of temperature and should have a value throughout most of the rubbery plateau region, of from $3.5 \times 10^5$ to $6.5 \times 10^5$ dynes per cm$^2$. More specifically, G' should have this value of from $3.5 \times 10^5$ to $6.5 \times 10^5$ dynes per cm$^2$ at the arithmetic average temperature of $T_g$ and $T_f$ i.e., at the temperature $(T_g + T_f)/2$ wherein $T_g$ and $T_f$ are in degrees centigrade. Still further, at this arithmetic average temperature, the function $\log_{10}$ G' versus temperature (where G' is expressed in dynes/cm$^2$ and temperature is in ° C.) should have a slope, $d(\log_{10} G')/d(T)$, which lies between -0.005 and -0.025.

It is equally important that the selected composition be capable of maintaining the above set out rheological properties throughout the expected shelf life and in use. Accordingly, it has been discovered that the composition will do so if the selection is made on the basis of the composition exhibiting essentially no substantial viscosity reduction when held, for a period of ninety hours at 350° C. (176.7° C.), in an air environment. By essentially no substantial viscosity reduction, it is meant that the viscosity immediately after the ninety hour period is no less than about 95% of the initial viscosity and preferably no less than about 97%, the viscosity being measured by use of a Brookfield viscometer.

EXAMPLE 1

A first series of adhesive formulations is prepared having the following compositions:

| COMPONENT | Weight % | Part per 100 parts Rubber |
|---|---|---|
| Sample 1 | | |
| Kraton G 1652 | 20.0 | 100.0 |
| Arkon P-85 | 52.4 | 262.0 |
| Tufflo 6054 | 25.6 | 128.0 |
| $TiO_2$ | 1.0 | 5.0 |
| Ethyl 330 | 1.0 | 5.0 |
| Sample 2 | | |
| Kraton G 1657 | 25.0 | 100.0 |
| Arkon P-85 | 52.1 | 208.0 |
| Tufflo 6056 | 20.9 | 84.0 |
| $TiO_2$ | 1.0 | 4.0 |
| Ethyl 330 | 1.0 | 4.0 |
| Sample 3 | | |
| Kraton G 1652 | 19.8 | 100 |
| Escorez 5280 | 59.5 | 300 |
| Shellflex 371 | 19.8 | 100 |
| Butyl Zimate | 0.6 | 3 |
| Ethyl 330 | 0.3 | 2 |

The Kraton G series rubbery polymers are A-B-A block copolymers having polystyrene end groups and a midblock of polyethylene polybutylene copolymer with varying molecular weights and varying weight percentages of end block polymeric groups as are defined hereinafter. Arkon P-85 is employed in the above composition as a tackifying resin and is a mixture of alicyclic, aliphatic, and unsaturated monosubstituted aromatic compounds having softening points of 85° C. The resin is obtained from the Arakawa Rinsan Kagaku Kogyo, K.K. company of Higashi-ku, Osakashi, Japan.

Tufflo 6054 and Tufflo 6056 are plasticizers, supplied by the Atlantic Richfield Oil Company, and comprises a mixture of paraffinic, naphthenic and aromatic hydrocarbons having an aromatic hydrocarbon weight % of about 13% and 5%, respectively, based on gel-clay analysis.

Ethyl 330 is an antioxidant available from the Ethyl Corporation and comprises 1,3,5-trimethyl-2,4,6 tris [3,5-di-tert-butyl-4-hydroxybenzil] benzene.

Escorez 5280 is a tackifying resin available from the Exxon Corporation and comprises a mixture of alicylic and aliphatic short chain hydrocarbons and a small amount of monosubstituted aromatic hydrocarbons. The softening point of the resin is approximately 85° C.

Shellflex 371 is a plasticizer available from the Shell Oil Company and comprises a mixture of paraffinic naphthenic and aromatic hydrocarbons. The aromatic weight percent is about 34%, by gel-clay analysis.

Butyl Zimate is an antioxidant available from the R. T. Vanderbilt Company and comprises Zinc di-n-butyl dithiocarbamate.

The above set out formulations are subjected to thermomechanical Spectrometer analysis by use of a Spectrometer manufactured by Rheometrics, Inc., of Union, N.J. The geometric mode chosen for these tests is parallel plates and the oscillation frequency is chosen to be 1.0 radians per second. The results of the rheological analysis is set out in Table 1, below.

The stability of the samples are tested by measuring the viscosity reduction, by use of a Brookfield viscometer when the sample has been subjected to a temperature 350° F. for ninety hours. These results are reported in Table 1.

The adhesive formulations are tested to determine their in-use performance with respect to the properties of tenacious bonding and clean release.

A sanitary napkin of the general construction of the Sure and Natural Maxishield Manufactured by Personal Products Co. of Milltown, N.J. is provided with a line of the adhesive composition of this invention. The napkin comprises a generally rectangular absorbent body having a body facing side and a garment facing side. A barrier sheet of polyethylene film is adhered to the garment facing side of the absorbent body and held in place with adhesive and an overwrapping tissue layer. The assembly is then enveloped in a generally rectangular cover of nonwoven material. The edges of the nonwoven material parallel to the longitudinal edges of the napkin overlaps on the garment facing side of the napkin. A rectangular line of the adhesive composition of this example is positioned to·overlie the overlapped portions of the cover. The line has a length of six inches (15.24 cm) and a width of ¾ of an inch (1.9 cm). The weight of adhesive composition applied is 370 milligrams per pad, uniformly distributed at a weight distribution of about 12.7 mg/cm$^2$.

To test the tenacity of the adhesive bond, a Fast Fabric Peel Test is performed using the Tag and Label Manufacturers Institute Peel and Release Tester manufactured by Testing Machines, Incorporated of Amityville, N.Y. Prior to the test, the sanitary napkin is conditioned for 16 hours at a temperature of 21° C. and a relative humidity of 65% together with a cotton woven fabric having 80 lines per inch in both the machine and cross direction, measuring 7 inches by 2½ inches and obtained from Test Fabric, Inc. of Middlesex, N.J. After conditioning the cotton fabric is adhered to the napkin and the napkin and fabric are pressed between two stainless steel plates for one minute at a peak load of 150 pounds. The pressure is released and after eighty minutes have passed, allowing the system to equalibriate, the cotton fabric is peeled from the napkin using the Tester at a peel rate of 1200 inches per min. and a peel angle of nominally 180°. The value is reported in grams of peak force per inch of width transverse to the peel direction.

Clean release is measured by conducting five sucessive peel tests as described above with the exception that the time between pressure release and the test is one minute instead of 80 minutes utilizing the same cotton fabric in each case. The weight gain of the fabric is determined and reported as mg of adhesive per cm$^2$ of adhesive area.

TABLE 1

| | SAMPLE | | |
|---|---|---|---|
| | 1 | 2 | 3 |
| RUBBERY POLYMER | | | |
| Weight % Polymer in Composition | 20 | 25 | 19.8 |
| Weight % Polystyrene end groups | 29 | 14 | 29 |
| Number Average Molecular | 98,000 | 105,500 | 98,000 |

TABLE 1-continued

| | SAMPLE | | |
|---|---|---|---|
| | 1 | 2 | 3 |
| Weight Average Molecular Weight | 109,500 | 135,700 | 109,500 |
| RHEOLOGY | | | |
| Glass Transition Temperature, °C. ($T_g$) | 8.0 | 0.0 | 5.0 |
| Flow Temperature, °C. ($T_f$) | 63.0 | 50.0 | 60.0 |
| $T_g - T_f$, °C. ($\Delta T$) | 55.0 | 50.0 | 55.0 |
| $(T_g + T_f)/2$, Tav, °C. | 35.5 | 25.0 | 32.5 |
| G', dynes/cm² at Tav | $4.0 \times 10^5$ | $6.0 \times 10^5$ | $6.0 \times 10^5$ |
| d(log $_{10}$G')/d(T) at Tav | −0.0074 | −0.0072 | −0.0098 |
| STABILITY | | | |
| % Viscosity Reduction | ~0 | ~0 | ~0 |
| IN-USE PERFORMANCE | | | |
| Equilibrium Peel, gm/in | 870 | 800 | 700 |
| Residue, mg/cm² adhesive area | None | None | None |

As is summarized in the above Table 1, the rubbery polymer varied significantly in its chemical properties such as number average molecular weight, weight average molecular weight and the weight percent of polystyrene end groups. Additionaly the weight percentage of rubbery polymer in the formulations varied over a significant range. This notwithtanding, the combination of these variables resulted in formulations, each of which conformed, with respect to their rheological properties, to the teachings of this invention. Further, each of the compositions conformed to the stability requirements set out herein.

Accordingly, the in use performance of these conforming adhesives is satisfactory. The equilibrium peel strength in each case weighs at least 700 gm/in, a value found to insure that a sanitary napkin, for example, will remain securely in place in use. This tenacous bonding is coupled with essentially no adhesive transfer to an undergarment fabric, these combined properties heretofore unexcelled with stable adhesive formulations of this kind.

COMPARATIVE EXAMPLE

To illustrate the advantages of this invention, a series of comparative samples were prepared having the following formulations:

| COMPONENT | Weight % | Parts per 100 Parts Rubbers |
|---|---|---|
| SAMPLE 4 | | |
| KRATON G 1652 | 15.0 | 100 |
| ARKON P-85 | 55.8 | 372 |
| TUFFLO 6054 | 27.2 | 181 |
| TiO₂ | 1.0 | 7 |
| Ethyl 330 | 1.0 | 7 |
| SAMPLE 5 | | |
| KRATON G 1650 | 14.9 | 100 |
| ARKON P-85 | 53.5 | 359 |
| TUFFLO 6054 | 29.7 | 199 |
| TiO₂ | 1.0 | 7 |
| Ethyl 330 | 1.0 | 7 |
| SAMPLE 6 | | |
| KRATON G 1650 | — | — |
| WINGTACK 95 | — | — |
| OTHER | — | — |

Sample 6 is a commercially available formulation whose composition is not totally known. Wingtack 95 is a tackifying resin available from the Goodyear Tire and Rubber Company and comprises a polymerized piperylene isoprene solid tackifier having a softening point of about 95° C.

The samples are tested for their rheological, stability and in-use performance properties in the manner set out in Example 1. The results are reported in Table 2 below.

TABLE 2

| | SAMPLE | | |
|---|---|---|---|
| | 4 | 5 | 6 |
| RUBBERY POLYMER | | | |
| Weight % Polymer in Composition | 15.0 | 14.9 | N/A |
| Weight % Polystyrene End Groups | 29.0 | 28 | 28 |
| Number Average Molecular Weight | 98,000 | 108,300 | 108,300 |
| Weight Average Molecular Weight | 109,500 | 123,900 | 123,900 |
| RHEOLOGY | | | |
| Glass Transition Temperature, °C. ($T_g$) | 10.0 | 6.0 | 6.0 |
| Flow Temperature, °C. ($T_f$) | 60.0 | 70.0 | 90.0 |
| $T_g - T_f$, °C. ($\Delta T$) | 50.0 | 64.0 | 84.0 |
| $(T_g + T_f)/2$, °C. (Tav) | 35.0 | 38.0 | 48.0 |
| G', dynes/cm² at TAV | $1.8 \times 10^5$ | $2.7 \times 10^5$ | $4.0 \times 10^5$ |
| d(log$_{10}$ G')/d(T) at $T_{av}$ | −0.0108 | 0.0 | 0.0 |
| STABILITY | | | |
| % Viscosity Reduction | ~0 | ~0 | 30 |
| IN-USE PERFORMANCE | | | |
| Equilibrium Peel, gm/in | 650.0 | 130 | 120 |
| Residue, mg/cm² area | $6.9 \times 10^{-2}$ | None | None |

As Table 2 indicates, the rubbery polymer weight percent, the percent polystyrene end groups end the molecular weights of the polymer are all within the range of the values for these parameters as set out in Table 1. This notwithstanding, these parameters are so combined in samples 4 through 6 as to produce rheological properties outside the range of those prescribed herein and, as is shown in Table 2, result in in-use performance which is substantially less satisfactory than the invention conforming compositions of samples 1-3.

Specifically, sample 4 exhibits a storeage modules G', which lies below the prescribed range of $3.5 \times 10^5$ to $6.5 \times 10^5$ dynes/cm² at the midtemperature of the rubbery plateau region, Tav. As a result, while the equilibrium peel value is close to satisfactory, the amount of residue is unacceptable.

Sample 5 exhibits a rubber plateau temperature interval, $\Delta T$, which is too long as well as a low G' at Tav. Additionally, the slope of the function log$_{10}$ G' vs. T at $T_{av}$ is too small. The results in in-use performance is insufficient equilibrium peel value.

Similarly, sample 7 exhibits a $\Delta T$ which is too great and a slope which is too small. The results again is insufficient peel value.

This sample also suffers from the drawback of insufficient stability in that the sample exhibited a viscosity reduction of 30% when held at 350° F. for ninety hours.

We claim:

1. A hot melt pressure sensitive adhesive composition comprising:
    an A-B-A- block copolymer wherein said B midblock comprises polyolefins and said A endblock comprises polystyrene and having a number average molecular weight of the individual A blocks of from about 7,000 to about 30,000;
    a tackifying resin present in the proportions of from about 200 to about 300 parts by weight per 100 parts by weight of said block copolymer;

a plasticizer present in the proportions of from about 80 to about 150 parts by weight per 100 parts by weight of said block copolymer;

said block copolymer, tackifying resin, and plasticizer, being chosen and being present in the proportions such that said adhesive composition has a glass transition temperature of the rubbery phase ranging from about 0° C. to about 10° C.;

a temperature difference between the glass transition temperature of the rubbery phase and the flow temperature ranging from about 45° C. to about 55° C.;

a storage modulus which is a monotonic decreasing function of temperature between the glass transition temperature of the rubbery phase and the flow temperature, said storage modulus having a value, at the arithmetic average temperature between the glass transition temperature of the rubbery phase and the flow temperature of from about $3.5 \times 10^5$ to $6.5 \times 10^5$ dynes/cm$^2$; and the function $\log_{10}$ of the storage modulus verses temperature at a temperature equal to the arithmetic average of the glass transition temperature of the rubbery phase and the flow temperature having a slope of from about $-0.005$ to about $-0.025$ where the temperature is in degrees centigrade and the storage modulus is in dynes/cm$^2$; and said adhesive composition exhibiting a viscosity reduction of less than 5% when maintained at 350° F. for ninety hours;

whereby said pressure-sensitive adhesive will exhibit a high equilibrium peel strength and a low adhesive transfer upon peeling.

2. The hot melt pressure-sensitive composition of claim 1 wherein said A-B-A block copolymer has end groups which comprise from about 10 to about 50 percent by weight of the block copolymer.

3. The hot melt pressure sensitive adhesive composition of claim 1 wherein the reduction in viscosity is less than about 2 percent.

4. The hot melt pressure-sensitive adhesive composition of claim 1 exhibiting in equilibrium peal strength greater than about 700 gms. per inch.

5. The hot melt pressure sensitive adhesive composition of claim 1 exhibiting a transfer of adhesive of less than $3 \times 10^{-2}$ milligrams per square inch of transfer area.

6. A sanitary napkin for adhering to the crotch portion of an undergarment comprising an absorbent body for absorbing body fluids and having a body facing side and a garment facing side;

a layer of hot melt pressure-sensitive adhesive composition overlying the at least a portion of the garment facing side;

said hot melt pressure-sensitive adhesive comprising:

an A-B-A- block copolymer wherein said B midblock comprises polyolefins and said A endblock comprises polystyrene and having a number average molecular weight of the individual A blocks of from about 7,000 to about 30,000;

a tackifying resin present in the porportions of from about 200 to about 300 parts by weight per 100 parts by weight of said block copolymer;

a plasticizer present in the proportions of from about 80 to about 150 parts by weight per 100 parts by weight of said block copolymer;

said block copolymer, tackifying resin, and plasticizer, being chosen and being present in the proportions such that said adhesive composition has a glass transition temperature of the rubbery phase of about 0° C. to about 10° C.;

a temperature difference between the glass transition temperature of the rubbery phase and the flow temperature of about 45° C. to about 55° C.;

a storage modulus which is a monotonic decreasing function of temperature between the glass transition temperature of the rubbery phase and the flow temperature, said storage modulus having a value, at the arithmetic average temperature between the glass transition temperature of the rubbery phase and the flow temperature of about $3.5 \times 10^5$ to $6.5 \times 10^5$ dynes/cm$^2$; and the function $\log_{10}$ of the storage modulus verses temperature at a temperature equal to the arithmetic average of the glass transition temperature of the rubbery phase and the flow temperature having a slope of from about $-0.005$ to about $-0.025$ where the temperature is in degrees centigrade and the storage modulus is in dynes/cm$^2$; and said adhesive composition exhibiting a viscosity reduction of less than 5% when maintained at 350° F. for ninety hours;

whereby said sanitary napkin may be applied to said undergarment and will exhibit a high equilibrium peel strength and a low adhesive transfer upon removal.

* * * * *